United States Patent [19]

Roth

[11] 4,057,060

[45] Nov. 8, 1977

[54] DISPOSABLE MEDICINAL APPLICATION APPARATUS

[75] Inventor: Richard C. Roth, Milltown, N.J.

[73] Assignee: Block Drug Company, Inc., Jersey City, N.J.

[21] Appl. No.: 630,185

[22] Filed: Nov. 10, 1975

[51] Int. Cl.² .......................... A61M 3/00; A61M 7/02
[52] U.S. Cl. .................................. 128/232; 128/247; 128/251; 206/364; 215/264; 222/83
[58] Field of Search ............... 128/224, 225, 227, 247, 128/248, 249, 250, 251, 261, 272, 232, DIG. 24; 206/222, 498, 223, 229, 364, 363; 222/82, 85, 81, 83, 83.5, 87, 88; 215/264

[56] References Cited

U.S. PATENT DOCUMENTS

| | | | |
|---|---|---|---|
| 2,746,647 | 5/1956 | Efford et al. | 206/229 X |
| 2,950,029 | 8/1960 | Winstead | 128/272 X |
| 3,006,341 | 10/1961 | Poitras | 128/272 X |
| 3,024,947 | 3/1962 | Jeynes, Jr. | 222/83.5 |
| 3,030,952 | 4/1962 | Elder | 206/229 X |
| 3,144,866 | 8/1964 | Ellis | 128/251 X |
| 3,255,923 | 6/1966 | Soto | 222/81 X |
| 3,321,070 | 5/1967 | Childs | 206/84 |
| 3,354,883 | 11/1967 | Southerland | 222/80 X |
| 3,402,855 | 9/1968 | Schroeder et al. | 222/83 |
| 3,589,362 | 6/1971 | Zamarra | 128/247 X |
| 3,613,955 | 10/1971 | Wetherell, Jr. | 206/222 X |
| 3,726,276 | 4/1973 | Schumann et al. | 128/251 X |
| 3,911,918 | 10/1975 | Turner | 128/227 |

Primary Examiner—J. Reed Fisher
Attorney, Agent, or Firm—Ostrolenk, Faber, Gerb & Soffen

[57] ABSTRACT

A disposable medicinal application apparatus for use in the administration of a medicinal fluid comprises sealed flexible bag means at least partially filled with a quantity of the fluid to be applied. The apparatus has a neck piece freely enclosed within the sealed bag means, the neck piece being manipulable against the interior surface of a portion of the bag means and the bag wall being stretched over the neck piece. A separate applicator member has a passage in communication with discharge means. Cooperative locking and lockable means are formed on the applicator member and the neck piece, respectively, to allow the applicator member to be snap-fitted and locked to the neck piece, with the bore of the neck piece and the passage of the applicator member in alignment. A portion of the bag wall is compressed between the exterior surface of the neck piece and the interior surface of the applicator member to form a fluid-tight seal therebetween. A portion of the applicator member comprises means for puncturing the bag wall to allow egress of the medicinal fluid through the aligned bore and passage of the cooperatively locked neck piece and applicator member.

7 Claims, 11 Drawing Figures

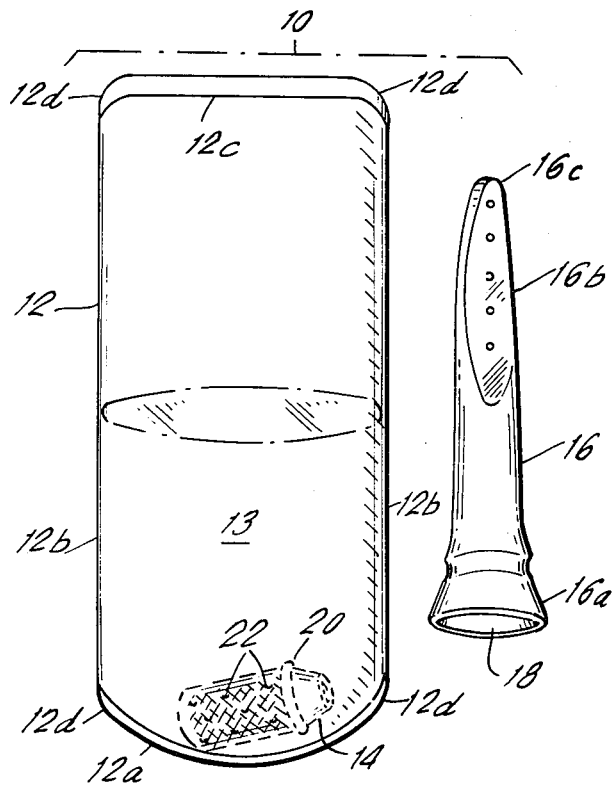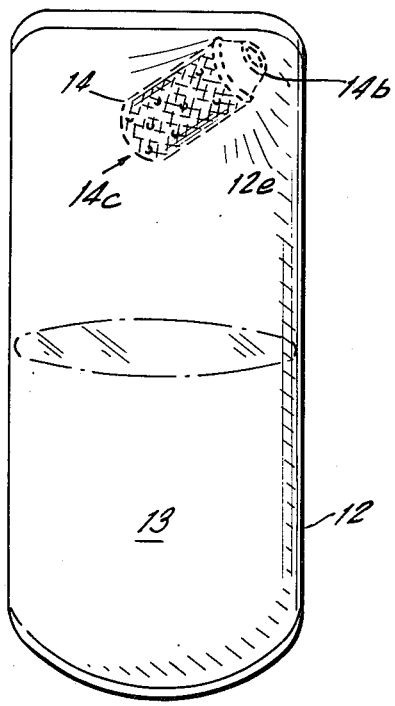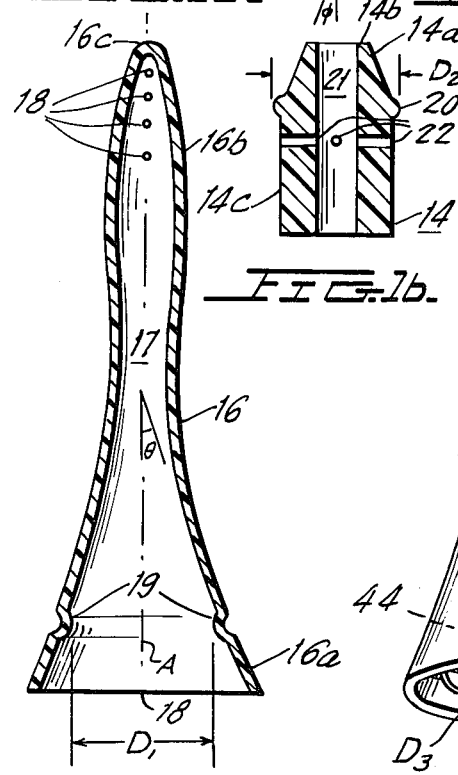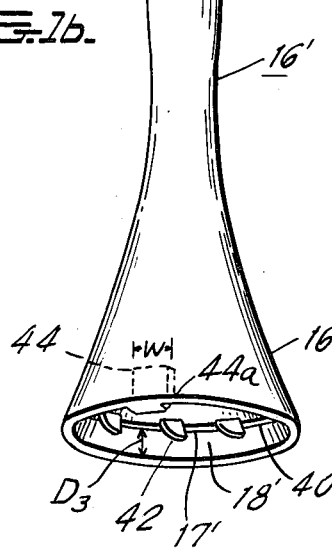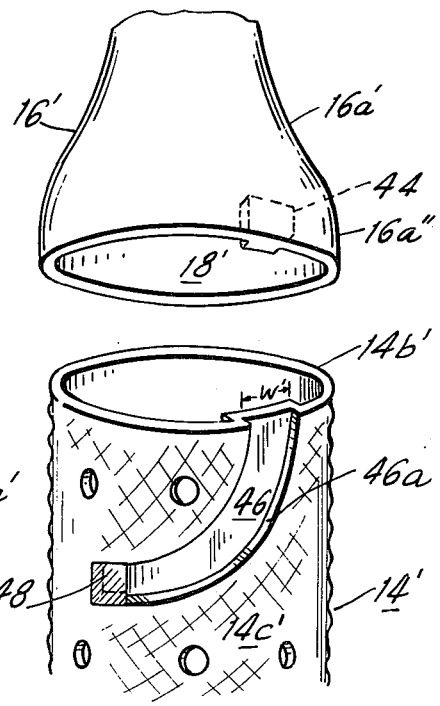

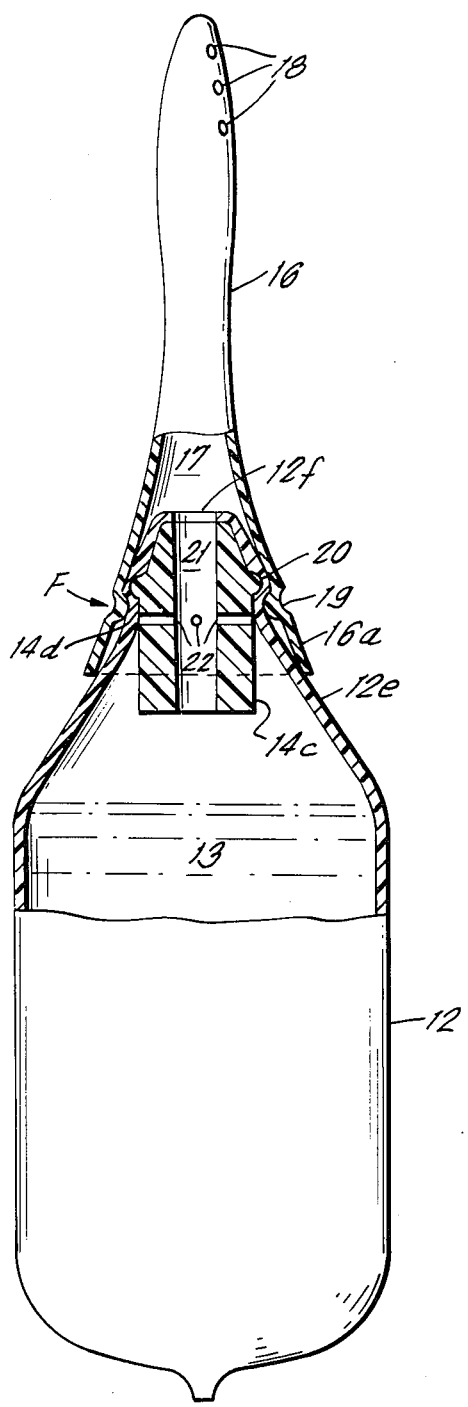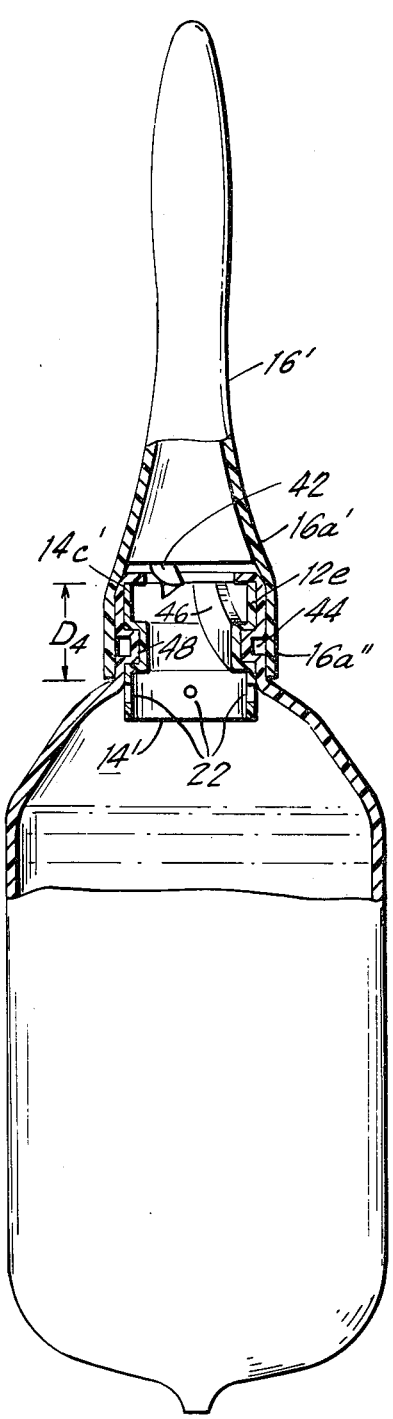

DISPOSABLE MEDICINAL APPLICATION APPARATUS

BACKGROUND OF THE INVENTION

This invention relates to apparatus for the administration of a medicinal solution and to the method for fabrication thereof, and more particularly to a novel disposable medicinal application apparatus of the pre-filled bag type.

There has recently been an increased demand for a apparatus usable in the administration of medicinal solutions, and in particular for the administration of douche solutions utilized in feminine hygiene. The conventional application apparatus is generally classifiable as either reusable or disposable apparatus. Apparatus in the reusable class must be refilled with a solution for each individual medicinal administration. The refill mechanism generally adds considerable bulk and cost to the apparatus while the refilling process tends to be messy and poses a question as to the ultimate cleanliness of the apparatus.

Apparatus of the disposable class is preferred, as it can be pre-filled at the manufacturer's facility to realize considerable savings in both bulk and cost. A high degree of applicator cleanliness is achieved because the refill mechanism is no longer required and the apparatus is packed in a shipping carton at the manufacturer's facility.

Among the problems encountered in disposable apparatus is the need to prevent undue stress on the solution-containing bag to prevent the rupture thereof at potentially weak points, and to assure a liquid-tight seal between the bag and an applicator tip to prevent leakage of the medicinal solution therefrom.

It is also desireable to fabricate and package the apparatus by automatic means to assure a high standard of cleanliness and uniformity.

BRIEF SUMMARY OF THE INVENTION

In accordance with the invention, disposable medicinal application apparatus, realizing the above stated goals, comprises a sealed bag containing, but not completely filled with, a quantity of the final medicinal solution; a neck piece having a longitudinal passage formed therethrough, the neck piece being freely enclosed within the sealed bag; and an applicator member having opposed first and second ends and having a longitudinal interior passage opening into at least one bore formed through the wall of the member adjacent to the first end thereof. Cooperating locking portions are formed on the exterior surface of the neck piece and the interior surface of the applicator member adjacent to the second end thereof to allow snap-fitted engagement therebetween.

The neck piece is manipulated against the interior surface of a portion of the sealed bag and the bag wall is stretched over the neck piece. The applicator member is snap-fitted over the stretched bag portion and the snap-lock members cooperate to compress the wall between the neck piece and applicator member to form a liquid-tight seal.

In a preferred embodiment, puncturing means are formed within the longitudinal passageway adjacent to an opposite end of the applicator member to puncture the bag wall and allow egress of medicinal solution only after the applicator member has been tightly snap-fitted to the cooperating neck piece.

In other preferred embodiments, the locking means includes a spiraling channel formed into the neck piece exterior surface and cooperating means radially inwardly extended from the interior surface of the applicator member to both snap- and twist-lock the applicator member to the neck piece with a portion of the bag wall compressed therebetween; a textured exterior surface for the neck piece to enhance friction fit and hence the quality of the liquid-tight seal; and radially extending passageways through the wall of the neck piece and the overlying bag wall to exit from the sealing area.

A method for fabricating the novel application apparatus includes providing a shipping container having open and closed ends, placing an applicator tip and an instruction sheet within the volume of the container, placing the closed end of a bag within the container and folding the open end of the bag down around the periphery of the open container end. The neck piece is placed within the bag and the bag is then parially filled with the final medicinal solution. The periphery of the open end of the bag is drawn up over the open end of the container and sealed; the sealed bag end is then placed within the container volume before the open end of the shipping container is closed with a container cap.

Accordingly, it is one object of the present invention to provide novel disposable medicinal application apparatus and a method for the fabrication thereof.

It is another object of the present invention to provide disposable medicinal application apparatus utilizing a pre-filled bag containing the medicinal solution and an applicator member which is joinable to the bag in a manner so as to prevent accidental leakage of the medicinal solution at the joint therebetween.

These and other objects of the present invention will become apparent from a reading of the following detailed description and the drawings.

BRIEF DESCRIPTION OF THE FIGURES

FIG. 1 is a plan view of one embodiment of disposable medicinal application apparatus in accordance with the principles of the present invention;

FIG. 1a is a cross-sectional view of one preferred embodiment of an applicator member for use as part of the apparatus of the present invention;

FIG. 1b is a cross-sectional view of one preferred embodiment of a neck piece for use with the application member of FIG. 1a;

FIG. 2 is a plan view of a neck piece-containing bag and illustrating the manner in which the neck piece is positioned prior to locking the applicator member thereto;

FIG. 4a is a partially-sectionalized plan view of the apparatus of FIG. 1 illustrating the manner in which a liquid-tight seal is formed;

FIG. 5a is a perspective view of another preferred embodiment of applicator member;

FIG. 5b is a perspective view illustrating the applicator member of FIG. 5a and a portion of another embodiment of a neck piece with which it is used;

FIG. 6 is a partially-sectionalized plan view of the assembled apparatus utilizing the neck piece and applicator members of FIGS. 5a and 5b.

DETAILED DESCRIPTION OF THE INVENTION

Figure 7:
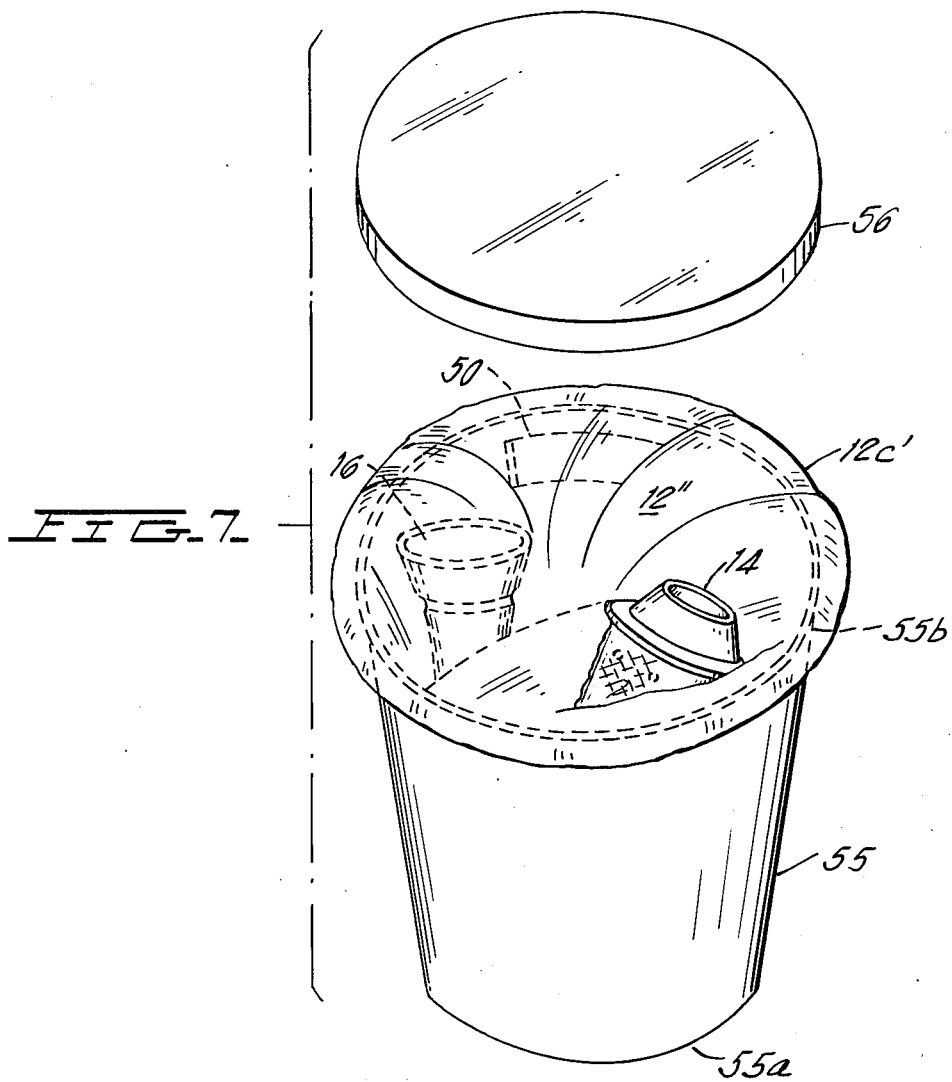
FIG. 7 is an exploded perspective view of the apparatus in its shipping container during the fabrication thereof and useful in understanding the method of fabrication.

Referring now to the Figures, disposable medicinal application apparatus 10 includes a bag 12 formed of a soft ductile material, such as a plastic film or the like, of reasonably heavy gauge. Bag 12 is preferably formed from a blown tube of the desired material and has a first end 12a initially sealed by a reliable sealing method, such as heat, r.f., impulse or the like. It should be understood that bag 12 may also be formed of a pair of overlaid portions of the bag material sealed along each of end 12a and at least one side edge 12b.

Bag 12 is at least partially, but not completely, filled with a predetermined quantity 13 of a final medicinal solution. A neck piece 14, to be more fully described hereinbelow, is placed within the bag before the remaining end 12c of the bag is sealed. Neck piece 14 is freely contained within the bag 12 without attachment to the bag wall. In a preferred embodiment, at least the corners 12d of top and bottom edges 12c and 12a, respectively, are sealed with a rounded configuration to prevent undue stress and subsequent seal failure as a result of hydraulic action when the bag material is placed under pressure; the rounded outside corners also eliminate sharp points from the bag, to increase the ease of application for the ultimate user.

An applicator member 16 is packaged with sealed bag 12. Applicator member 16 is preferably formed of a soft material, such as vinyl or the like, and has a flared proximal end 16a and a tapering distal end portion 16b with rounded distal tip 16c. An axial bore 17 (FIG. 1a) within applicator member 16 extends from proximal end opening 18 along the axial length of the member. A plurality of passageways 18 extend radially through the wall of the distal portion 16b of the applicator member to allow outflow of the solution entering the member through open end 18 and flowing through axial bore 17 toward tip 16c. Passageways 18 may be formed with a wide range of angular orientations with respect to the axis of rotation A of the applicator member to form a particular spray pattern best suited by the end use. Locking means 19 is positioned on an interior surface of proximal applicator portion 16a and cooperates, in a manner to be more fully explained, with lockable means 20 formed upon the exterior surface of neck piece 14. Proximal end 16a is of generally conical shape, as defined by a central angle $\theta$ to the axis of revolution of the member, and gradually merges into tapering distal nozzle portion 16b.

Neck piece 14 (FIG. 1b) is of generally cylindrical shape and has a forward end 14a having a frusto-conical shape, tapering inward at an angle $\phi$ towards the axis of rotation of the neck piece. In a preferred embodiment, the convergence ange $\phi$ of the neck piece 14 and the flare angle $\theta$ of the proximal portion 16a of the applicator member 16 are substantially equal.

Neck piece 14 has an axial bore 21 extended completely therethrough to form an annular surface on its forward end 14b. As previously mentioned, lockable means 20 is formed upon the exterior surface of neck piece 14.

In one preferred embodiment, locking means 19 includes a radially-inward extending bead formed completely about the interior surface of applicator member flared portion 16a to reduce the diameter thereof to a predetermined value $D_1$. Lockable means 20 includes a radially-outward extending bead formed completely about the circular periphery of neck piece 14 at the point where frusto-conical portion 14a begins its convergence towards the axis of rotation of neck piece 14; the maximum bead diameter $D_2$ of neck piece 14 is predeterminately selected to be substantially equal to or greater than the minimum bead diameter $D_1$ of locking means 19.

Figures 3, 4:
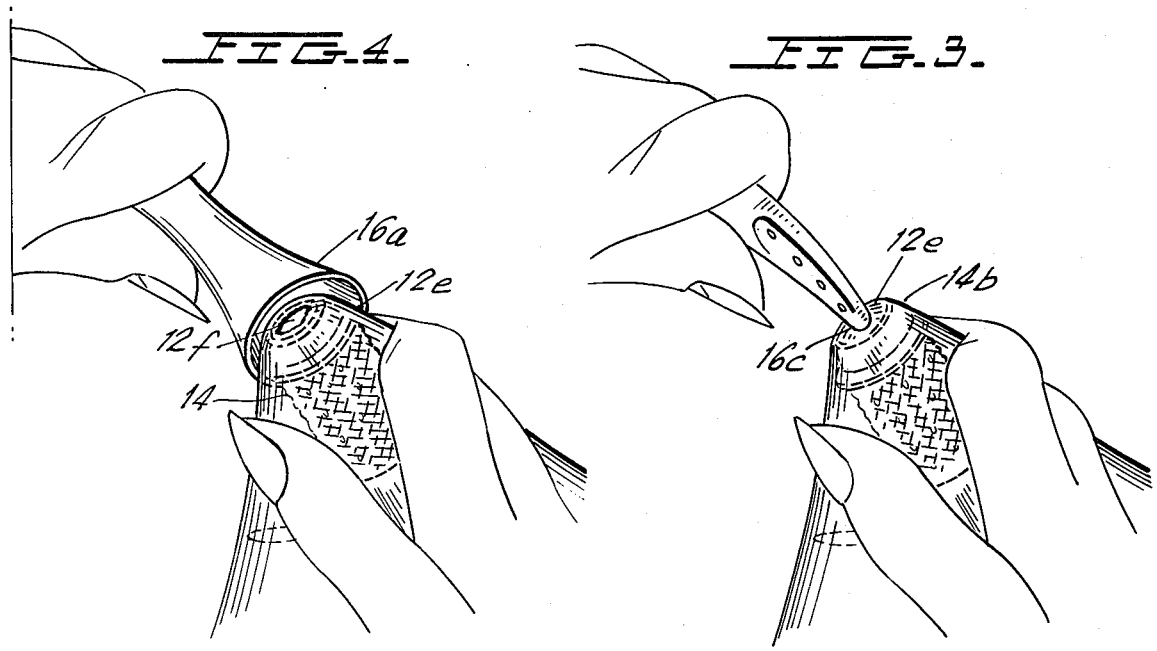
FIG. 3 is a pictorial diagram illustrating the rupturing of the bag wall over the neck piece bore.
FIG. 4 is a pictorial illustrating the positional relationship between bag, neck piece and applicator member immediately prior to snap-locking the apparatus components together.

In use, sealed bag 12, applicator member 16 and instruction sheet 50 are removed from a pre-packed shipping container 11 (FIG. 7). The "free-floating" neck piece 14 is manipulated into the volume of bag 12 free of solution 13 (FIG. 2) and the forward end 14b of the neck piece is placed against the interior surface of bag wall 12e. The bag wall and neck piece are grasped together and a portion of the bag wall 12e is stretched across annular end surface 14b and the open end of the neck piece bore 21 (FIG. 3).

The rounded distal tip portion 16c of applicator member 16 is utilized to puncture the stretch bag wall portion 12e and form an aperture 12f therethrough. I have found that a bag wall having a thickness at least as large as 0.001 inches can be adequately ruptured in this fashion due to the stretching of the wall material while the puncture is being made. The applicator member 16 is then reversed (FIG. 4) to allow flared proximal portion 16a to be resiliently forced over the forward end of neck piece 14 and the overlying portion of bag wall 12e, until locking means 19 is snap-fittingly locked over lockable means 20.

In the assembled apparatus (FIG. 4a), the bag wall portion 12e is compressed between the locked annular beads of locking means 19 and lockable means 20. Neck piece bore 21, aperture 12f and applicator member bore 17 are held in axial alignment to allow egress of the final medicinal solution 13 to passageways 18 upon application of pressure to bag 12. Advantageously, the material selected for applicator member 16 has resilient properties causing sufficient force to be applied in the direction of arrow F to form a liquid-tight seal between applicator member 16 and bag wall 12 in the annular region 14d of neck piece 14 adjacent to locking means 19 and lockable means 20.

In a preferred embodiment, a plurality of passageways 22 extend radially through the wall of neck piece 14 to allow outflow of any liquid trapped between bag wall 12e and neck piece exterior surface 14c during the locking procedure. Neck piece exterior surface 14c may also advantageously be provided with a roughened surface (FIG. 2), formed by scoring, cross-hatching, pebbling or the like, to further assure that the bag material and neck piece surface "lock" together when firmly grasped during formation of the liquid-tight seal.

After the dosage of medicinal solution 13 has been squeezed from bag 12, the assembled apparatus 10 is disposed of in some suitable manner. Applicator member 16 may be unlocked from neck piece 14 and removed to be retained for reuse.

In another preferred embodiment, an applicator member 16' is formed of a somewhat stiffer material, such as a rubber or semi-stiff vinyl composition or the like, and includes an annular shelf 40 extending radially inward from the interior surface of the applicator member at a distance $D_3$ from the plane of proximal end opening 18'. A plurality of puncture means 42, such as cutter teeth or the like, are formed upon shelf 40 for rupturing the stretched portion of bag wall 12e at the time the applicator member is fastened to the neck piece. As the forward end 14b' of a neck piece will extend some predetermined distance $D_4$ into the bore 17' of applicator member 16', the length of puncure means 42 is selected consistent with the primary function of piercing the bag wall and yet be significantly less than distance $D_3$ whereby the risk of accidental injury to the user's fingers is substantially reduce. This embodiment also enables at least a partially liquid-tight seal to be established before the bag is punctured to minimize the possibility of inadvertent discharge of medicinal solution 13 before the applicator member is firmly locked to the bag and neck piece.

Applicator member 16' also includes at least one male lug 44 upon its interior surface at the periphery of proximal end 16a'. Lug 44 has a width W and a thickness T.

Hollow cylindrical neck piece 14' has a curved track 46 formed into its exterior surface 14c' starting at the forward end 14b' and spiraling inward along a portion of the exterior surface. A locking formation 48 having substantially the same width W' and a generally square shape is formed into the wall of neck piece 14' at the end of track 46. The depth of formation 48 below exterior surface 14c' is greater than the depth of track 46 below the same surface. The width W' of track 46 is greater than the width W of lug 44 to allow passage of the lug when a portion of bag wall 12e is compressed around the lug in the track. A corner 44a of lug 44 is removed to allow the lug to be positioned within track 46 and to be slidably maneuvered along the length of the curved track toward formation 48 when applicator member 16' is pressed toward and rotated about neck piece 14'. It should be understood that track 46 may twist in either direction or may be a linear groove formed in the axial direction in surface 14c' and having formation 48 disposed at the end thereof, although the linear arrangement will not provide as high quality a seal as will a spiral arrangement.

In use, top surface 14b' of neck piece 14' is positioned against a portion of bag wall 12e and is pressed until the bag wall is stretched taut. Open end 18' of applicator member 16' is placed over the overlaid bag wall and neck piece combination and each of lugs 44 is aligned with and places into an associated track 46. Bag wall 12e is caught between lug 44 and track 46 and is further compressed as applicator member 16' increasingly covers neck piece 14'. Corner portion 44a allows lug 44 to slide along the bottom wall 46a of the track until lug 44 enters recessed formation 48. The resilient properties of the material chosen for applicator member 16' causes each lug 44 to snap into recess 48 and lock the applicator member to the neck piece with bag wall 12e securely compressed therebetween. As previously described, the length of each cutter tooth 42 is selected to pierce the portion of bag wall 12e stretched across top surface 14b' of neck piece 14' only after lug 44 has moved at least some distance along track 46, thereby stretching the bag wall portion to a greater extent and, more especially, compressing the bag wall against the exterior side surface 14b' of the neck piece to form a liquid-tight seal before the bag wall is ruptured, thus preventing any possibility that the contents of the sealed bag may be spilled during the securing of the applicator member to the bag and neck piece.

In another preferred embodiment, the proximal end portion 16a" is formed with an annular wall generally parallel to the axis of rotation of the applicator member 16' to resiliently provide more force and a greater contact area with the exterior surface of neck piece 14' to compress a greater portion of the bag wall and provide an even higher quality liquid-tight seal.

The disposable medicinal application apparatus 10, which may be advantageously utilized to irrigate, cleanse or medicate various parts of the body and may be of differing sizes as required for the intended end usage, is fabricated at the manufacturer's facility by inserting an applicator member 16 and an instruction sheet 50 into the volume of an open ended shipping container 55 (FIG. 7). An open ended bag 12" is placed with its sealed end 12a adjacent the bottom 55a of the container and the periphery of open end 12c' is folded over the top edge 55b of the container. A neck piece 14 is dropped into bag 12" though its open end 12c' and the bag is then partially filled with a measured quantity of a premixed medicinal solution 13. The periphery of open end 12c' is then lifted above open container end 11b and is sealed in a suitable manner to close the upper end 12c of the bag. The sealed upper end is placed within the volume of container 11 and a shipping cap 56 having interior dimensions selected to cooperate with the dimensions of container open end 55b, is placed over the open end of the container to enclose the contents of container 55 and is then sealed by suitable means. Advantageously, all of the above mentioned fabrication steps may be carried out in an automated manner in the manufacturer's facility, to provide disposable application apparatus having both low cost and a high degree of cleanliness.

There has just been described a novel disposable medicinal application apparatus utilizing a flexible bag pre-filled with a final quantity of a medicinal solution and having novel means for joining a neck piece to a free-floating neck piece within the bag. A method for the fabrication of this novel disposable medicinal application apparatus for use in the administration of a premixed medicinal solution is also disclosed.

While several preferred embodiments of the present invention have been described, many variations and modifications will now become apparent. Therefore, this invention is to be limited, not by the specific disclosure herein, but only by the appended claims.

What is claimed is:

1. Apparatus for application of a medicinal fluid, comprising:
   sealed bag means at least partially filled with said medicinal fluid;
   a neck piece having a first end and having a generally axial bore formed therethrough in communication with said first end, said neck piece being freely enclosed within said sealed bag means and adapted for manipulation of said first end against an interior surface of said bag means;
   an applicator member having opposed first and second ends, said applicator member including discharge means at said first end and having a passage between said discharge means and said second end; said applicator member also including means for piercing a wall of said bag means to form an opening therein in communication with said bore of said neck piece;
   lockable means formed upon an exterior surface of said neck piece adjacent said first end and comprising at least one channel formed to a selected depth into the exterior surface of said neck piece and extended from said first end of said neck piece;

locking means formed upon an interior surface of said applicator member within said passage and adjacent to said second end and comprising a similar number of lug means radially extending inward into the passage of said applicator member adjacent to said second end; each channel in said neck piece being adapted to slidingly receive an associated lug means and to securely lock said lug means in said channel with a portion of said bag means compressed between said channel and said lug means;

said locking and lockable means being adapted to cooperatively lock said neck piece and said applicator member together with a portion of the wall of said bag means compressed between said neck piece and said applicator member to form a substantially fluid-tight seal;

wherein said lockable means further comprises a recess formed at the end of said neck piece channels furthest from said first end of said neck piece, said recess having a greater depth into said neck piece than the depth of said channel to snaplockingly receive an associated lug means.

2. Apparatus as set forth in claim 1, wherein said applicator member passage has a diameter at said second end greater than the largest dimension of said neck piece in a plane transverse to said bore, to allow at least a portion of said neck piece adjacent to said first end to enter into said applicator member passage when said lockable and locking means are locked together.

3. Apparatus as set forth in claim 1, wherein said sealed bag has first and second ends, at least one of said ends having arcuate corners to relieve hydrostatic pressure thereon to prevent rupture of said bag means.

4. Apparatus as set forth in claim 1, wherein at least a portion of the exterior surface of said neck piece is roughened to cause said bag means and said neck piece exterior surface to "lock" together during formation of said fluid-tight seal.

5. Apparatus as set forth in claim 1, wherein said neck piece further includes at least one radially disposed passage between said bore and said exterior surface, to allow fluid to be drained away from said neck piece exterior surface during formation of said fluid-tight seal.

6. Apparatus as set forth in claim 1, wherein said piercing means is positioned within said passage of said applicator member to puncture the wall of said bag means only after said applicator member has been partially positioned over said neck piece and has at least partially compressed a portion of said bag means against said neck piece, thereby preventing discharge of said fluid from said apparatus during the formation of said seal.

7. Apparatus as set forth in claim 1, wherein said discharge means comprises at least one passageway formed through the wall of said applicator member between said passage and the exterior surface of said applicator member, the number and angular relationship between each discharge opening and the axis of said passageway being selected to achieve a desired discharge spray shape.

* * * * *